(12) United States Patent
Richard

(10) Patent No.: US 9,526,742 B2
(45) Date of Patent: Dec. 27, 2016

(54) USE OF EPIGENOME-MODIFYING COMPOUNDS FOR THE TREATMENT OF GENETIC MUSCULAR DISEASES LINKED TO A PROTEIN-CONFORMATIONAL DISORDER

(71) Applicant: GENETHON, Evry (FR)

(72) Inventor: Isabelle Richard, Corbeil Essonnes (FR)

(73) Assignee: GENETHON, Evry (FR)

( * ) Notice: Subject to any disclaimer, the term of this patent is extended or adjusted under 35 U.S.C. 154(b) by 0 days.

(21) Appl. No.: 14/407,211

(22) PCT Filed: Jul. 16, 2013

(86) PCT No.: PCT/FR2013/051705
§ 371 (c)(1),
(2) Date: Dec. 11, 2014

(87) PCT Pub. No.: WO2014/013184
PCT Pub. Date: Jan. 23, 2014

(65) Prior Publication Data
US 2015/0141361 A1 May 21, 2015

(30) Foreign Application Priority Data
Jul. 19, 2012 (FR) ..................... 12 57021

(51) Int. Cl.
*A61K 31/706* (2006.01)
*A61K 31/167* (2006.01)
*G01N 33/50* (2006.01)
*A61K 31/7068* (2006.01)

(52) U.S. Cl.
CPC .......... *A61K 31/706* (2013.01); *A61K 31/167* (2013.01); *A61K 31/7068* (2013.01); *G01N 33/5061* (2013.01); *G01N 2440/10* (2013.01); *G01N 2440/12* (2013.01); *G01N 2500/10* (2013.01); *G01N 2800/2878* (2013.01)

(58) Field of Classification Search
CPC A61K 31/706; A61K 31/167; G01N 33/5061; G01N 2800/2878; G01N 2500/10; G01N 2440/10; G01N 2440/12
USPC .............................. 514/43, 575; 435/18, 6.13
See application file for complete search history.

(56) References Cited

FOREIGN PATENT DOCUMENTS

| WO | 00/20582 A2 | 4/2000 |
|---|---|---|
| WO | 03/066885 A2 | 8/2003 |
| WO | 2004/050076 A1 | 6/2004 |
| WO | 2007/014327 A2 | 2/2007 |
| WO | 2008/009802 A2 | 1/2008 |
| WO | 2011/068522 A1 | 6/2011 |

OTHER PUBLICATIONS

Minetti et al. Functional and morphological recovery of dystrophic muscles in mice treated with deacetylase inhibitors. Nature Medicine 12(10):1147-1150, 2006.*
Qureshi et al. Long non-coding RNAs in nervous system function and disease. Brain Res 1338:20-35, 2010.*
Gastaldello et al. Inhibition of Proteasome Activity Promotes the Correct Localization of Disease-Causing alpha-Sarcoglycan Mutants in HEK-293 Cells Constitutively Expressing beta-, gamma-, and delta--Sarcoglycan. Am J Pathol 173:170-181, 2008.*
Ghoshal et al. 5-Aza-Deoxycytidine Induces Selective Degradation of DNA Methyltransferase 1 by a Proteasomal Pathway That Requires the KEN Box, Bromo-Adjacent Homology Domain, and Nuclear Localization Signal. Mol Cell Biol 25:4727-4741, 2005.*
Consalvi et al. Histone Deacetylase Inhibitors in the Treatment of Muscular Dystrophies: Epigenetic Drugs for Genetic Diseases. Mol Med 17:457-465, 2011.*
Bushby, "The Limb-Girdle Muscular Dystrophies—Proposal for a New Nomenclature," 30th and 31st ENMC International Workshops, Naarden, The Netherlands, Held Jan. 6-8, 1995, *Neuromusc. Disord.* 5(4):337-343, Abstract (1995).
Danièle et al., "Ins and outs of therapy in limb girdle muscular dystrophies," *Int J Biochem Cell Biol.* 39(9):1608-1624. Abstract (2007).
Duclos et al., "Progressive Muscular Dystrophy in α-Sarcoglycan-deficient Mice," *The Journal of Cell Biology* 142(6):1461-1471 (1998).
Egelhofer et al., "An assessment of histone-modification antibody quality," *Nat Struct Mol Biol.* 18(1):91-93 (2011).
Fujita et al., "Two endoplasmic reticulum-associated degradation (ERAD) systems for the novel variant of the mutant dysferlin: ubiquitin/proteasome ERAD(I) and autophagy/lysosome ERAD(II)," *Human Molecular Genetics* 16(6):618-629 (2007).
Kazantsev et al., "Therapeutic application of histone deacetylase inhibitors for central nervous system disorders," *Nature* 7:854-868 (2008).
Kefi et al., "Phenotype and sarcoglycan expression in Tunisian LGMD 2C patients sharing the same del521-T mutation," *Neuromuscul Disord.* 13(10):779-787 (2003).
Le et al., "Beta-sarcoglycan: characterization and role in limb-girdle muscular dystrophy linked to 4q12," *Nat Genet.* 11(3):257-265 (1995).
Nigro, "Molecular bases of autosomal recessive limb-girdle muscular dystrophies," *Acta Myol.* 22(2):35-42 (2003).
Ong et al., "Chemical and/or biological therapeutic strategies to ameliorate protein misfolding diseases," *Current Opinion in Cell Biology* 23:231-238 (2011).
Othmane et al., "Evidence for Linkage Disequilibrium in Chromosome 13-Linked Duchenne-Like Muscular Dystrophy (LGMD2C)," *Am. J. Hum. Genet.* 57:732-734 (1995).
Passos-Bueno et al., "Evidence of genetic heterogeneity in the autosomal recessive adult forms of limb-girdle muscular dystrophy following linkage analysis with 15q probes in Brazilian families," *J Med Genet* 30:385-387 (1993).

(Continued)

*Primary Examiner* — Clinton Brooks
*Assistant Examiner* — Yih-Horng Shiao
(74) *Attorney, Agent, or Firm* — Seed IP Law Group LLP

(57) ABSTRACT

A pharmaceutical composition including at least one epigenome-modifying compound, for a use thereof in the treatment of genetic muscular diseases linked to a conformational disorder of at least one protein, said disorder causing the cellular degradation of the protein.

2 Claims, 1 Drawing Sheet

(56) References Cited

OTHER PUBLICATIONS

Figure 1:
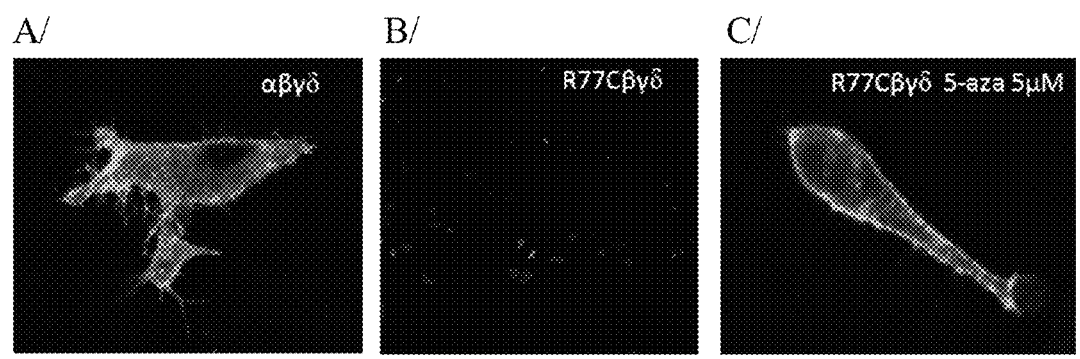

Passos-Bueno et al., "Linkage analysis in autosomal recessive limb-girdle muscular dystrophy (AR LGMD) maps a sixth form to 5q33-34 (LGMD2F) and indicates that there is at least one more subtype of AR LGMD," *Human Molecular Genetics* 5(6):815-820 (1996).
Piccolo et al., "A founder mutation in the γ-sarcoglycan gene of Gypsies possibly predating their migration out of India," *Human Molecular Genetics* 5(12):2019-2022 (1996).
Soheili et al., "Rescue of Sarcoglycan Mutations by Inhibition of Endoplasmic Reticulum Quality Control is Associated with Minimal Structural Modifications," *Human Mutation* 33:429-439 (2012).
Todorova et al., "C283Y mutation and other C-terminal nucleotide changes in the gamma-sarcoglycan gene in the Bulgarian Gypsy population," *Hum Mutat* 15(5):479 Abstract (2000).

\* cited by examiner

USE OF EPIGENOME-MODIFYING COMPOUNDS FOR THE TREATMENT OF GENETIC MUSCULAR DISEASES LINKED TO A PROTEIN-CONFORMATIONAL DISORDER

FIELD OF THE INVENTION

The present invention relates to the treatment of genetic muscular diseases linked to a protein conformational disorder and where the protein having the conformational disorder undergoes a cellular degradation. Particularly targeted diseases are for example sarcoglycanopathies, dysferlinopathies, anoctaminopathies (linked to an anoctamin-5 deficiency) and dystrophies associated with a FKRP ("Fukutin-Related Protein") anomaly.

More specifically, it advocates identifying and using agents modifying the epigenome as medications for the treatment of such diseases.

STATE OF THE ART

Pathologies due to an anomaly of the muscular fibers are generally called myopathies and are characterized by a destabilization and a degeneration of the muscles most often resulting in an alteration and in a loss of motor functions.

Over 80 rare myopathies of genetic origin have been identified. Their transmission may be dominant, recessive, or linked to the X chromosome. Each of the forms has a low prevalence (from 1/200,000 to 1/8,500), even if the cumulative frequency reaches approximately 1/3,000.

Among such pathologies, the most complex group is that of progressive muscular dystrophies, which comprises at least 25 different pathologies which may be divided into proximal muscular dystrophies, called girdle dystrophies, and into distal muscular dystrophies.

Proximal muscular dystrophies are characterized by a progressive and selective atrophy of certain muscles of the scapular and pelvic girdles and distal muscular dystrophies are characterized by an initial impairment of the hand, feet, forearm, or leg muscles.

The genetic disorder results in a cyclic process of degeneration/regeneration of the muscular tissue resulting in a pathological transformation thereof. On a histological level, this process is characterized by fibers having a centralized nucleus, indicative of the necrosis and regeneration steps, macrophage and adipose infiltrations, and a secondary fibrosis.

The clinical symptoms may be very heterogeneous according to the type of pathology, ranging from a simple fatigue to the loss of walking ability, a strength decrease which usually goes along with a muscular atrophy (Daniele et al., 2007). Such pathologies may thus have a strong impact on the patients' quality of life due to the muscle loss capable of resulting in death by respiratory or cardiac impairment.

More specifically, proximal muscular dystrophies or limb girdle muscular dystrophies (LGMD) are classified according to their transmission mode: LGMD1 for dominant forms and LGMD2 for recessive forms (Bushby and Beckmann, 1995).

The common characteristics of LGMD1s are: an onset of the symptoms in the young adult or adult age, a slow development, a low frequency of loss of the walking ability and relatively normal creatine kinase values. These dominant forms are less frequent than recessive forms, amounting to less than 10% of all LGMDs (Nigro, 2003) with only one or a few families reported for each type.

To date, sixteen forms of recessive autosomal limb girdle muscular dystrophies (LGMD2) have been identified and annotated with the addition of a capital letter (LGMD2A to 2P). All the genes responsible for such dystrophies have been identified.

The corresponding proteins have various locations and roles.

In a still more complex manner, it should be noted that mutations in a number of genes implied in LGMD2s are also associated with a distal-type clinical presentation. As an example, the following can be mentioned:

dysferlin which, when mutated, may also cause a Miyoshi myopathy;
anoctamin 5 which, when mutated, may also cause a Miyoshi-like type 3 myopathy;
titin which, when mutated, may also cause a tibial muscular dystrophy (TMD).

Among LGMD2s, sarcoglycanopathies are genetic diseases due to mutations in the sarcoglycan genes. Such proteins, by the number of 4, belong to a complex associated with the dystrophin present at the membrane of the muscle cell and which plays an essential role in the protection of the muscular fiber during contractions.

Thus, the following forms of sarcoglycanopathies have been listed:

LGMD2C, caused by a mutation in the gene encoding γ-sarcoglycan (Ben Othmane et al., 1995);
LGMD2D, caused by a mutation in the gene encoding α-sarcoglycan (Passos-Bueno et al., 1993);
LGMD2E, caused by a mutation in the gene encoding β-sarcoglycan (Lim et al., 1995); and
LGMD2F, caused by a mutation in the gene encoding δ-sarcoglycan (Passos-Bueno et al., 1996).

Responsible mutations in each of these genes could be identified: Thus, the most frequent mutation in LGMD2D is the substitution of arginine at position 77 by a cysteine (R77C). A specific mutation in the γ-SG gene, C283Y, at the root of LGMD2C, can be frequently encountered in the Gypsy population in Europe (Piccolo et al., 1996; Todorova et al., 1999). Another mutation in the γ-SG gene, de1521T, can be almost exclusively encountered in Tunisian families (Kefi, et al., 2003). Patients from the Amish community in the USA, where LGMD2E is frequent, carry mutation T151R (Duclos, et al., 1998; Lim et al., 1995).

In any case, there currently exists no really efficient remedial treatment for such diseases. Although kinesitherapy brings a comfort highly appreciated by the patients, the latter are mainly taken charge of by various medications and/or techniques aiming at improving the patients' quality of life.

In relation with the treatment of sarcoglycanopathies, document WO 2008/009802 has advocated the use of class-I α-mannosidases. In this context, it has been shown that a number of mutations in the sarcoglycan genes resulting, not in a loss of function of the protein, but in a degradation of the abnormally-conformed protein by the cell quality control system. Thus, the advocated inhibitors, directed against this system, would prevent the degradation of the mutated protein, which then finds a new functional membrane localization.

There however is an obvious need to develop new therapeutical approaches to take charge of genetic muscular diseases such as sarcoglycanopathies.

SUMMARY

Thus, a totally novel therapeutical approach is provided in the context of the present invention. Indeed, the Applicant has shown that it is possible to restore the functionality of a muscular protein having a conformational disorder, that is, a misfolding, by means of a compound modifying the epigenome.

More specifically and according to a first aspect, the present invention thus relates to a pharmaceutical composition comprising at least one compound modifying the epigenome, for a use thereof in the treatment of genetic muscular diseases linked to a conformational disorder of at least one protein, said anomaly causing the cellular degradation of the protein.

In other words, a composition comprising a compound modifying the epigenome should be used to prepare a medication intended for the treatment of genetic muscular diseases linked to a conformational disorder of at least one protein causing the cellular degradation thereof. The invention thus relates a method of treating genetic muscular diseases linked to a conformational disorder of at least one protein causing the cellular degradation thereof, comprising administering, at an efficient dose, a composition comprising a compound modifying the epigenome.

Said composition may further contain any compound or excipient which may be acceptable, particularly pharmaceutically. It may further comprise other active principles intended to treat the same pathology or another pathology. According to a specific embodiment, the compound(s) modifying the epigenome are the only active principles of the composition.

It may also be envisaged to associated, in the same composition, at least two compounds modifying the epigenome of different nature, to be administered simultaneously or at different times.

The administration route may as well be intramuscular, loco-regional, or intravenous, or even subcutaneous, intraperitoneal, or oral.

The administration mode, the administered dose, as well as the administration frequency are determined on a case by case basis, according to conventional protocols known by those skilled in the art.

"Epigenome" designates all the transmissible and possibly reversible biochemical signals which are associated with the genes to govern the expression thereof and thus ensure the execution of the genetic program linked to the activation and to the inactivation of these genes with no modification of the DNA sequence of a given differentiated cell.

Thus, even though the DNA sequence which forms the genes is identical in all the cells of a same individual, the proteins coded by these genes may be generated at different times or locations according to the epigenetic marks which are present on the genes.

The biochemical support of the epigenome is multiple and complex and implies:
  modifications at the DNA level;
  modifications at the histone level;
  the participation of certain proteins, such as polycombs;
  the participation of non-coding RNAs, of small size (microRNAs) and of large size (long non-coding RNAs).

In other words, a compound modifying the epigenome implemented in the context of the invention is a modulator of an epigenetic effector, that is, capable of at least partially modulating the expression and/or the activity thereof. "Modulator" means an activator (or inductor) as well as an inhibitor (or suppressor).

Such compounds may be of any nature, for example proteins, peptides, antibodies, chemical molecules, or nucleic acids (antisense oligonucleotides, siRNA, shRNA, ribozymes, . . . ).

According to a first embodiment, the expression and/or production level of the epigenetic effector is modulated (decreased or increased) by the concerned compound. This may be easily tested by those skilled in the art, particularly due to the following techniques:
  expression level of the Northern blot or PCR transcript;
  protein production level by detection by means of appropriate antibodies (Western blot or ELISA).

According to another embodiment, the epigenetic effector is generated and its activity is modulated (increased or decreased) by the compound in presence. In this case, this activity is quantified by means of an appropriate test according to the effector.

As to the nature of the compounds modifying the epigenome, the first level of the epigenetic control is known to concern the methylation of DNA, which occurs at the CpG dinucleotides and is established very soon during the development. It particularly results from the concerted action of three DNA methyltransferases (or DNMT).

Thus, according to a specific aspect, the compound modifying the epigenome may be an inhibitor of the methylation of DNA, particularly an inhibitor of DNA methyltransferases. This class of molecules is particularly adapted for in vitro applications.

This category comprises, among others:
  nucleoside analogues: they are incorporated into the replicating DNA. They thus inhibit the methylation of DNA and reactivate silent genes. It may be:
    5-azacytidine (or 5-aza), having formula:

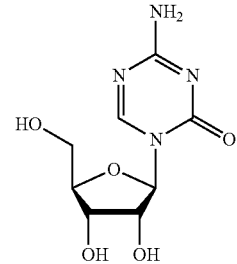

5-aza-2'-deoxycytidin ou decitabin, having formula:

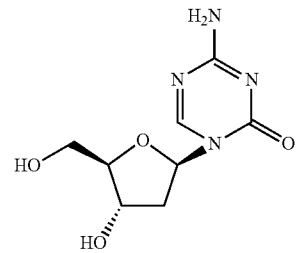

zeularmn;
  non-nucleoside analogues: they inhibit DNMTs by blocking the active site of the enzyme or by attaching to the CpG islands of DNA, thus preventing the binding of DNMTs to the DNA. It may be:
    procainamid;
    procain;
    epigallocatechin-3 gallate (EGCG);
  antisense oligonucleotides:
    DNMT1 ASO;

hydralazine, having formula:

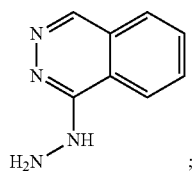

SGI110 (S110), having formula:

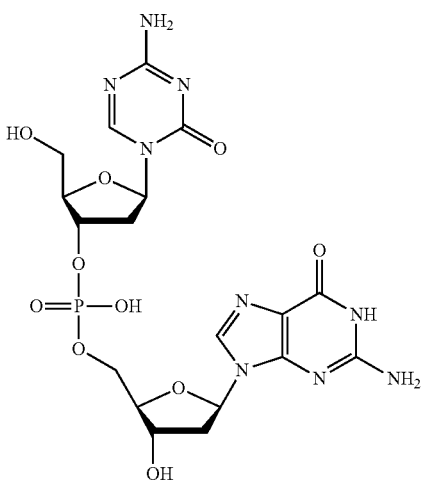

As a variation and preferably for in vivo applications, the compound modifying the epigenome is an inductor or an activator of the demethylation of DNA.

Generally, the ability of a compound to modulate the methylation of DNA can easily be tested: The methylation profile of DNA can be determined by a treatment of the DNA with bisulfate, which converts non-methylated cytosines into uracil but does not affect methylcytosines. Different methods based on direct sequencing, pyrosequencing, PCR, or hybridization may then be used to differentiate alleles.

Thus, due to this simple test, DNA methylation inhibitors or activators, capable of being used in the context of the present invention, can easily be identified.

Another level of action relates to covalent modifications of histones. Preferentially, such modifications concern: the acetylation of lysine residues, the methylation of lysine residues and of arginines, the phosphorylation of threonine and serine residues, the ubiquitination and the sumoylation of lysine residues.

Now, such modifications at the histone level may as well have a positive or a negative effect on the gene expression. The compound of interest may be of activator as well as of inhibitor type.

It is further possible to act on the histone modification enzymes either directly at the level of their activity, or genetically at the level of their expression.

In practice, it is possible to analyze the post-transcriptional modifications of histones, and thus to evaluate the impact of a compound of interest, by the well known Western Blot or ELISA techniques, implementing a panel of antibodies specific of histone modifications (Egelhofer et al., 2011).

As an example, and as already mentioned, it is possible to modulate the histone acetylation level. Now, the latter results from the activity of two antagonistic enzymes: histone desacetylases (HDAC), resulting in a repressed chromatin, and histoneacetyltransferases (HAT) which allow the gene expression.

Thus, and according to a specific aspect of the invention, the compound modifying the epigenome may be an inhibitor of desacetylase histones (HDAC).

It should be noted that there exist several classes of HDAC inhibitors according to their inhibition mode and to the category of HDACs that they target. Histone desacetylation inhibitors comprise:

hydroxamic acids or salts thereof:
trichostatin A (TSA);
alpha compound 8;
MC1568;
Tubucin;
suberoylanilide hydroxamic acid (SAHA or vorinostat), having formula:

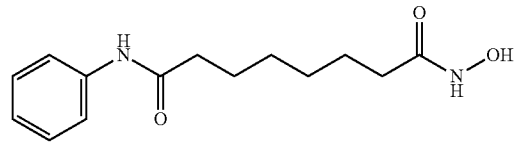 [SMILES: O=C(CCCCCCC(=O)Nc1ccccc1)NO]

cyclic tetrapeptides and depsipeptides:
trapoxin B;
apicidin;
benzamides:
entinostat (MS-275), having formula:

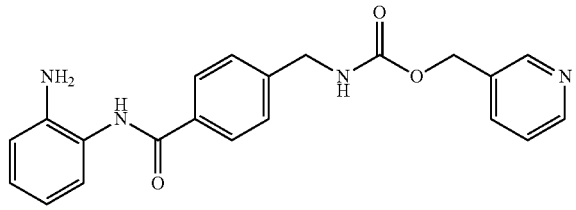 [SMILES: Nc1ccccc1NC(=O)c1ccc(CNC(=O)OCc2cccnc2)cc1]

CI-994;
106
Mocetinostat (MGCDO103)
electrophilic ketones:
trifluoromethyl ketones;
α-cetoamides;
aliphatic acid compounds:
phenylbutyrate, having formula:

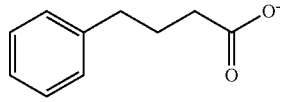 [SMILES: O=C([O-])CCCc1ccccc1]

valproic acid;
valproic acid;
belinostat (PXD101);
LAQ 824;
Panobinostat (LBH589);
the other molecules:
nicotinamide;
dihydrocoumarin;
naphthopyranone;
2-hydroxynaphaldehydes;
10-hydroxy-2-decenoic acid (10HDA);
Abexinostat (PCI-24781);
SB939;
Resminostat (4SC-201);
Givinostat (ITF2357);

CUDC-101;
AR-42;
CHR-2845;
CHR-3996;
4SC-202;
CG200745;
ACY-1215;
Sulforaphane;
Kevetrin;
Apicidin;
Sodium butyrate;
(−)-Depudecin;
Sirtinol;
N-Hydroxy-1,3-dioxo-1H-benz[de]isoquinoline-2(3H)-hexanamide or Scriptaid;
The hydroxamate derivative of butyric acid;
Isobutyramide;
CBHA (m-carboxycinnamic acid bishydoxyamide);
HC toxin;
M344 (4-dimethylamino-N-(6-hydroxycarbamoyl-hexyl) benzamide);
Nullscript (4-(1,3-dioxo-1H,3H-benzo[de]isoquinolin-2-yl)-N-hydroxybutanamide);
PCI-34051, having formula:

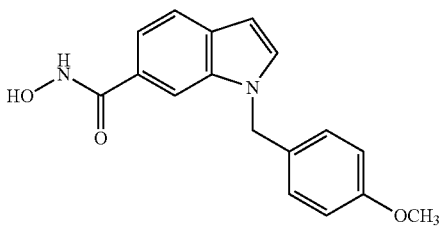 [SMILES: COc1ccc(Cn2ccc3ccc(C(=O)NO)cc32)cc1]

The chemical formulas of a number of these inhibitors are described in document Kazantsev and Thompson (Nature Reviews Drug Discovery, vol. 7, n° 10, 2008, 854-866). Further, a method of screening HDAC inhibitors is for example described in document WO 03/066885.

Advantageously, and for this class of compounds, the inhibitor used is SAHA.

Further, inhibitors of the methylation of histones may be:
SL11144, having formula:

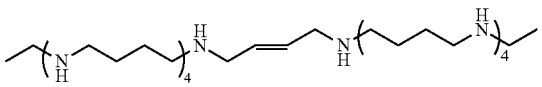

DZNep (3-Deazaneplanocin: inhibitor of S-adenosylhomocysteine hydrolase), having formula:

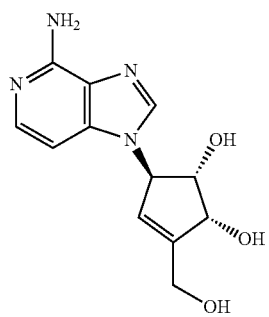 [SMILES: Nc1nccc2c1ncn2[C@@H]1C=C(CO)[C@@H](O)[C@H]1O]

A third control level may be exerted at the level of the PRC complex. Indeed, proteins from the polycomb group (PcG) are chromatin factors known to maintain the repressed transcriptional state of their target genes during the development. These factors act in the form of large multimeric complexes called Polycomb Repressive Complex (PRC) which bind to the DNA, at the level of regulating sequences called PcG response elements (PRE) to repress the genes by methylation. Indeed, PRC complexes also contain an intrinsic histone methyltransferase (HMTase) activity and repress the expression by the methylation of histones.

In the context of the present invention, any modulator of the PRC complex may be used. Polycomb proteins may for example be targeted, particularly inhibited or inactivated at the level of their expression by means of an antisense or by exon skipping. The expression or the activity of polycomb proteins may be monitored by the following conventional techniques: Western Blot expression level; binding to the DNA by gel mobility shift or chromatin precipitation.

Finally, the implication in the control of the expression of the genes of non-coding RNAs, microRNAs, and long non-coding RNAs, has been underlined.

MicroRNAs (miRNAs) are a class of non-coding RNAs of approximately 22 nucleotides which negatively modulate the gene expression in post-transcriptional manner. By binding by complementarity to the target RNA, they will result either in degrading this RNA, or in inhibiting the translation thereof. miRNAs may further influence epigenetic mechanisms by controlling the DNA methylation and the modifications of histones by recruitment of complexes at the level of the corresponding nascent transcript.

Another type of epigenetic actors are long non-coding RNAs (lncRNAs). They are transcribed at the level of gene or intergene sequences and have no or few open reading frames. These RNAs may target the chromatin or different aspects of the transcription by associating with different factors (transcription activators or repressors) as well as destabilize or, on the contrary, stabilize a coding RNA in the cytoplasm.

Thus, according to another aspect, the compound modifying the epigenome may be a modulator of non-coding RNAs, particularly of miRNAs and lncRNAs. The compound may play the role of a "sponge", that is, decrease the number of copies of the targeted non-coding RNA (for example, a complementary sequence or an antisense), as well as that of a "mimic", that is, increase the number of copies of the targeted non-coding RNA (for example, a vector carrying the miRNA).

It should be noted that in known fashion, the effect of a compound on the expression of a non-coding RNA can be easily analyzed, for example by Northern Blot or by quantitative RT-PCR.

Advantageously, the compound modifying the epigenome used in the context of the invention is an activator or an inhibitor:
of DNA methylation; or
of the modification of histones; or
of the PRC complex; or
of non-coding RNAs, advantageously microRNAs, and/or of long non-coding RNAs.

A number of currently available compounds are listed hereabove, particularly SAHA. However, this list cannot claim to be exhaustive. Thus, any compound capable of modulating the epigenome, particularly via the above-mentioned mechanisms, may be used in the context of the invention.

As already mentioned, the present invention relates to the treatment of genetic muscular diseases linked to a conformational anomaly of at least one protein causing the cellular degradation thereof.

Genetic diseases are, by definition, diseases resulting from one or a plurality of mutations in one or a plurality of genes.

Advantageously, the present application aims at monogenic diseases, that is, diseases linked to a single gene, in the case in point that coding the protein having a conformational disorder.

The mutations responsible for the conformational disorder of the resulting protein may be point mutations. However, the conformational disorder may be linked to mutations which are larger than points, for example, the deletion of a codon in the gene which codes a protein which is still active if it is not degraded.

Advantageously, the present invention aims at recessive muscular pathologies.

As already mentioned, the present invention aims at muscle pathologies, advantageously those affecting the skeletal muscles but also the heart muscle, advantageously the skeletal muscles.

In the context of the invention, "conformational disorder of at least one protein" or "protein conformational disorder" means the fact that the protein causing the disease is misfolded, due to the presence of at least one mutation in the gene encoding it, said disorder causing the degradation of said protein by the cell. The targeted pathologies can thus be easily identified, for example, by means of antibodies directed against the mutated protein. Indeed, even if it is correctly expressed (which may be verified at the transcript level), it is not detected by means of such an antibody, since it is degraded.

In the context of the invention, it has been shown that the degradation by the muscular cells of the proteins with the conformational disorder is controlled by epigenetic mechanisms. Thus, the provided solution relies on the use of compounds modifying the epigenome to avoid the degradation of mutated proteins, to ensure their addressing in the final cellular compartment, and thus to restore a normal phenotype.

According to a specific aspect, the protein having the conformational disorder and submitted to the cellular degradation is a protein of the membrane or associated with the membrane, possibly integrated in a protein complex.

Advantageously, the genetic muscular disease linked to a protein conformational disorder is a progressive muscular dystrophy, of proximal as well as of distal type.

Among progressive muscular dystrophies, the following diseases may particularly be mentioned:
  sarcoglycanopathies, that is, α-sarcoglycanopathy or LGMD2D linked to an α-sarcoglycan defect, β-sarcoglycanopathy or LGMD2E linked to a β-sarcoglycan defect, γ-sarcoglycanopathy or LGMD2C linked to a γ-sarcoglycan defect, or δ-sarcoglycanopathy or LGMD2F linked to a δ-sarcoglycan defect;
  dysferlinopathies (LGMD2B or Miyoshi myopathy) linked to a dysferlin defect;
  anoctaminopathies (LGMD2L or Miyoshi type 3 myopathy) linked to an anoctamin 5 defect;
  girdle myopathy with a FKRP or LGMD2I, linked to a defect of the FKRP ("fukutin-related protein").

More generally, the targeted diseases are selected from the following group:
  progressive muscular dystrophies:
    implying dysferlin (DYSF)
    implying γ-sarcoglycan
    implying α-sarcoglycan
    implying β-sarcoglycan
    implying δ-sarcoglycan
    implying anoctamin 5 (Ano5)
    implying the fukutin related protein (FKRP)
    implying fukutin (FKTN)
    implying protein-O-mannosyltransferase 1 (POMT1)
    implying protein-O-mannosyltransferase 2 (POMT2)
    implying protein-O-linked mannose β1,2-acetylglucosaminyl-transferase (POMGT1)
    implying caveolin 3 (Cav3)
    implying UDP-N-acetyl glucosamine 2-epimerase (GNE)
  congenital muscular dystrophies (CMD):
    implying α-dystroglycan (DAG1)
    implying laminin alpha-2 (LAMA2)
    implying like-glycosyltransferase (LARGE)
    implying collagen 6A1, 6A2, or 6A3
    implying selenoprotein 1 (SEPN1)
    implying integrin alpha7 (ITGA7)
    the ryanodine receptor (RYR)
  other diseases affecting the skeletal or heart muscle, possibly associated with impairments of other organs:
    arrhythmogenic right ventricular cardiomyopathy implying transmembrane protein 43 (TMEM43)
    type 4 liposdystrophy muscular dystrophy implying polymerase I and the transcript release factor (PTRF)
    the chondrodystrophic myotonia or Schwartz Jampel Syndrome implying heparan sulfate (HSPG2)
    the Danon disease implying the lysosomal-associated membrane protein 2 (LAMP2)
    Fibrodysplasia ossificans progressiva implying the type I activin A receptor (ACVR1).

For a same disease, different mutations may affect the same gene and be responsible for the poor configuration of the encoded protein. Thus, and as examples for sarcoglycanopathies, the main point mutations listed to date are listed in document WO 2008/009802.

In the context of the present application, the feasibility of the invention has for example been demonstrated in relation with the R77C mutation of α-sarcoglycan. The proteins carrying a E262K mutation in sub-unit 8 or a Q11E mutation in sub-unit β3 may also favorably respond to the advocated treatment.

As adapted, the mutated protein causing the disease is not dystrophin and the pathology to be treated is not the Duchenne muscular dystrophy (DMD) or the Becker muscular dystrophy (BMD), where the dystrophin is truncated, and not degraded since it is misfolded as in the invention.

Other methods or uses may result from the present invention:

According to another aspect, the invention relates to a method of identifying or evaluating the efficiency of a compound modifying the epigenome, which comprises the steps of:
  placing a cell producing a misfolded protein causing a genetic muscular disease in contact with said compound;
  determining the rate of correctly folded protein, advantageously by localization of the protein in the cell.

According to the invention and advantageously, the protein misfolding causes its degradation by the cell.

The production by the cell of the misfolded protein causing a genetic muscular disease may be obtained by transfection of the cell by means of the mutated gene encoding said protein.

The misfolded protein causing a genetic muscular disease may be a sarcoglycan causing a sarcoglycanopathy. More advantageously still, it is a α-sarcoglycan, for example, a α-sarcoglycan carrying a R77C mutation. In any case, this protein may be used as a positive control in the above-described method, since it has been demonstrated, in the present disclosure, that such a mutated protein favorably responds to a compound modifying the epigenome.

Advantageously, the cell and the compound are placed in contact with each other for several minutes, or even several hours.

The rate of correctly folded proteins is correlated to the efficiency of the tested compound as an epigenome-modifying compound. This rate is advantageously determined by detection, or even localization, of the protein or of the protein complex to which it belongs. Preferably, the detection of the protein or of the protein complex is performed by immunohistochemistry by means of antibodies directed against the concerned protein or against one of the proteins of the protein complex to which it belongs.

As a variation, the protein of interest or one of the proteins of the complex of interest may be marked, particularly by fluorescence, and then detected by microscopy or by sorting. This solution is advantageous since the detection step is less weighty than immunological detection. It is however important to verify that the fusion protein (protein of interest+marker) does not disturb the forming of the protein complex.

In the case where the protein or the protein complex is detected, or even localized in its final cellular compartment, it is concluded that the tested compound is an efficient compound for the modification of the epigenome.

Advantageously, the method is implemented in parallel:
on cells expressing the non-mutated protein as a positive control of the protein localization;
by carrying out an incubation in the absence of the tested compound, such a control enabling to conclude as to the possible effect of the tested compound.

According to another aspect, the present invention aims at a method of identifying a compound for the treatment of genetic muscular diseases linked to a conformational disorder of at least one protein causing the cellular degradation thereof, comprising evaluating the epigenome modification potential of the compound.

Thus, the invention also aims at a method of identifying a compound for the treatment of genetic muscular diseases linked to a conformational disorder of at least one protein causing the cellular degradation thereof, comprising the steps of:
placing a cell producing a misfolded protein causing a genetic muscular disease in contact with said compound;
determining the rate of correctly folded protein.

According to another aspect, the invention relates to a method of identifying genetic muscular diseases linked to a conformational disorder of at least one protein causing the cellular degradation thereof, comprising the steps of:
placing a cell capable of producing a misfolded protein causing a muscular genetic disease in contact with a compound modifying the epigenome;
determining the rate of correctly folded protein.

This embodiment comprises testing cells, advantageously muscle cells, of a patient capable of being affected by a genetic muscular disease linked to a conformational disorder of at least one protein causing the cellular degradation thereof. As a variation, the patient's gene, suspected to carry the mutation(s), is transfected into a cell to perform the in vitro test.

If the patient is effectively affected, the protein having a conformational disorder is expected not to be detectable, since it has been degraded. This may easily be tested as described hereabove, particularly by means of antibodies directed against said protein.

In the presence of the compound modifying the epigenome, it is expected for the rate of correctly folded protein to be increased and for the protein to be detectable, particularly in the detection test implemented at the previous step.

If, in fact, the rate of correctly folded protein increases along with the addition of the compound modifying the epigenome, it can be concluded that it effectively is a genetic muscular disease linked to a conformational disorder of the tested protein, causing the cellular degradation thereof.

More generally and according to another aspect, the invention relates to a method of production by a cell of a protein, possibly recombinant, in an active configuration comprising placing the cell in contact with a compound modifying the epigenome.

EXAMPLES OF EMBODIMENT

The invention and the resulting advantages will better appear from the following embodiments, in relation with the accompanying drawings. The latter are however by no means limiting.

The invention is further illustrated in relation with α-sarcoglycanopathy linked to the R77C mutation in α-sarcoglycan and in the presence of 5-azacytidine inhibitors (or 5-aza, an inhibitor of DNA methylation) and Saha (for "SuberoylAnilide Hydroxamic Acid", an inhibitor of histone desacetylases).

FIG. 1: Immunohistochemical marking of the α-sarcoglycan protein (α-SG) in quadriinfected HER 911 human cells:
A/ by means of non-mutated α-SG
B/ by means of α-SG carrying the R77C mutation
C/ by means of α-SG carrying the R77C mutation and in the presence of 5-μM 5-aza.

Figure 2:
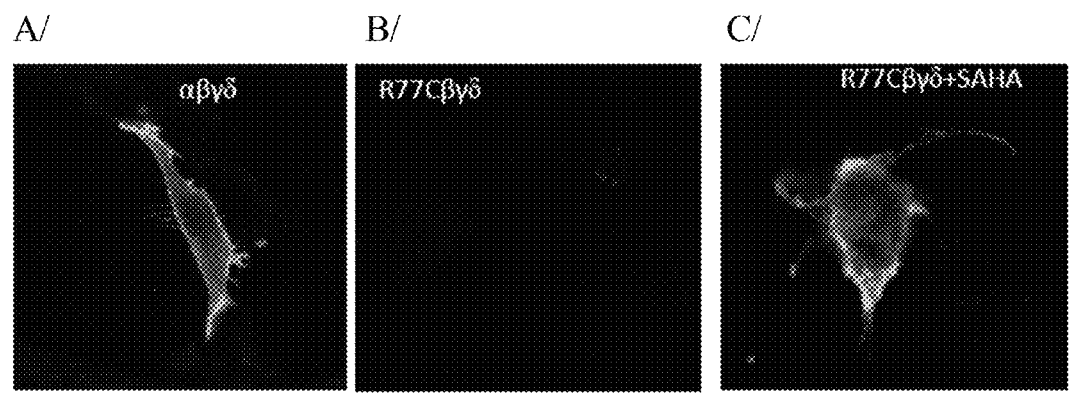

FIG. 2: Immunohistochemical marking of the α-sarcoglycan protein (α-SG) in quadriinfected HER 911 human cells:
A/ by means of non-mutated α-SG
B/ by means of α-SG carrying the R77C mutation
C/ by means of α-SG carrying the R77C mutation and in the presence of 1-μM SAHA.

1/MATERIALS AND METHODS 1.1 Cell Cultures, Transfections, and Treatments

HER-911 ("Human Embryonic Retinoblast") cells have been inoculated in vials and cultivated up to a 80% confluence in Dulbecco's modified Eagle's+GlutaMAX (Gibco, Invitrogen) medium containing 10% of fetal calf serum, 0.01 mg/ml of gentamicin, and 1% MEM Non Essential Amino Acids (Gibco, Invitrogen). The cells have been maintained in a humidified atmosphere with 5% C02, at 37° C.

The HER-91 cells have been transfected by means of 12 μl of Fugene.6 Transfection Reagent (Roche) for 2 μg of plasmid (0.5 μg of each of the 4 sarcoglycan (SG) constructions for HER-911 cells). The plasmids expressing the SG, pcDNA3.V5-his_hα-SG, pcDNA3.V5-his_hβ-SG, pcDNA3.V5-his_hγ-SG, and pcDNA3.V5-his_hδ1-SG (transcriptional type-1 variant), are plasmids where the expression of the coding sequence of the respective sarcoglycans is under control of the CMV promoter.

After 48 h, the cells have been treated for 24 h with 5 μM of 5-aza-2'-deoxycytidine or 1 μM of SAHA (Suberoylanilide hydroxamnic acid).

1.2 Immunofluorescence

The HER-911 cells have been fixed by incubation with 3.7% of formaldehyde for 15 min at room temperature. If necessary, a permeabilization has been performed by using 0.2% Triton X-100 for 20 min. After having been saturated with 20% fetal calf serum for 30 min, the cells have been incubated with primary antibodies at adapted dilutions (in PBS) for 1 h at room temperature. A monoclonal murine antibody specific for α-SG (NCL-A-SARC) is available from Novocastra. The cells have been washed 3 times with PBS and then incubated for 1 h with secondary antibodies diluted by 1/1,000 in PBS. Finally, the cells have been washed in PBS, mounted by using a Vectashield Mounting Medium with DAPI (Vector, H-1200), and then examined with a confocal immunofluorescence microscope (Leica).

2/RESULTS

HER 911 human cells have been quadri-transfected with plasmids coding β-, γ-, and δ-sarcoglycans and a plasmid coding either non-mutated α-sarcoglycan (FIG. 1A and FIG. 2A), or R77C mutated α-sarcoglycan (FIGS. 1B and 1C; FIGS. 2B and 2C).

An immunomarking has then been performed on the non-permeabilized cells by using an antibody directed against the extracellular portion of the α-sarcoglycan, which enables to visualize the protein only at the cellular membrane level and thus to compare the addressing of the mutated protein with that of the normal protein.

Conversely to the non-mutated form of the α-sarcoglycan protein (FIGS. 1A and 2A), mutated form R77C of this protein is not addressed to the membrane of HER 911 cells (FIGS. 1B and 2B). The cell treatment with 5-azacytidine (FIG. 1C) or with SAHA (FIG. 2C), restores the membrane localization of the R77C-mutated protein.

The principle underlying the present invention has thus been confirmed in vitro on a model of quadritransfected cells enabling to reconstitute the complex on sarcoglycans, by analyzing the membrane addressing of the complex. The use of drugs modifying the epigenome, that is, 5-azacytidine, a DNA methylation inhibitor, or Saha, an inhibitor of desacetylase histones, has enabled to reconstitute the complex at the membrane.

BIBLIOGRAPHY

Ben Othmane K, Speer M C, Stauffer J, Blel S, Middleton L, Ben Hamida C, Etribi A, Loeb D, Hentati F, Roses A D, "Evidence for linkage disequilibrium in chromosome 13-linked Duchenne-like muscular dystrophy (LGMD2C)." Am J Hum Genet. 1995 September; 57(3):732-4.

Bushby, K. M., and J. S. Beckmann, 1995, "The limb-girdle muscular dystrophies—proposal for a new nomenclature". Neuromuscul Disord. 5:337-43.

Daniele, N., I. Richard, and M. Bartoli, 2007, "Ins and outs of therapy in limb girdle muscular dystrophies." Int JBiochem Cell Biol. 39:1608-24.

Duclos, F., V. Straub, S. A. Moore, D. P. Venzke, R. F. Hrstka, R. H. Crosbie, M. Durbeej, C. S. Lebakken, A. J. Ettinger, J. van der Meulen, K. H. Holt, L. E. Lim, J. R. Sanes, B. L. Davidson, J. A. Faulkner, R. Williamson, and K. P. Campbell, 1998, "Progressive muscular dystrophy in alpha-sarcoglycan-deficient mice." J Cell Biol. 142: 1461-71.

Egelhofer et al., Nat. Struct. Mol. Biol. 2011 January; 18(1): 91-3.

Kefi M, Amouri R, Driss A, Ben Hamida C, Ben Hamida M, Kunkel L M, Hentati F. "Phenotype and sarcoglycan expression in Tunisian LGMD 2C patients sharing the same del1521-T mutation Neuromuscul Disord." 2003 December; 13(10):779-87.

Lim L E, Duclos F, Broux O, Bourg N, Sunada Y, Allamand V, Meyer J, Richard I, Moomaw C, Slaugther C, 1995, "Beta-sarcoglycan: characterization and role in limb-girdle muscular dystrophy linked to 4q12." Nat Genet. November; 11(3):257-65.

Nigro, V., 2003, "Molecular bases of autosomal recessive limb-girdle muscular dystrophies." Acta Myol. 22:35-42.

Passos-Bueno M R, Richard I, Vainzof M, Fougerousse F, Weissenbach J, Broux O, Cohen D, Akiyama J, Marie S K, Carvalho A A, 1993, "Evidence of genetic heterogeneity in the autosomal recessive adult forms of limb-girdle muscular dystrophy following linkage analysis with 15q probes in Brazilian families.>> J Med Genet. May; 30(5):385-7.

Passos-Bueno M R, Moreira E S, Vainzof M, Marie S K, Zatz M., 1996, "Linkage analysis in autosomal recessive limb-girdle muscular dystrophy (AR LGMD) maps a sixth form to 5q33-34 (LGMD2F) and indicates that there is at least one more subtype of A R LGMD." Hum Mol Genet. June; 5(6):815-20.

Piccolo, F., M. Jeanpierre, F. Leturcq, C. Dode, K. Azibi, A. Toutain, L. Merlini, L. Jarre, C. Navarro, R. Krishnamoorthy, F. M. Tome, J. A. Urtizberea, J. S. Beckmann, K. P. Campbell, and J. C. Kaplan, 1996, "A founder mutation in the gamma-sarcoglycan gene of gypsies possibly predating their migration out of India." Hum Mol Genet. 5:2019-22.

Todorova A, Ashikov A, Girdlecheva O, Tournev I, Kremensky I. "C283Y mutation and other C-terminal nucleotide changes in the gamma-sarcoglycan gene in the Bulgarian Gypsy population." Hum Mutat. 1999; 14(1):40-4. Erratum in: Hum Mutat 2000; 15(5):479.

The invention claimed is:

1. A method for treating a genetic muscular disease that is linked to a conformational disorder of at least one protein causing the cellular degradation of the protein, wherein said disease is selected from the group consisting of sarcoglycanopathies, dysferlinopathies, anoctaminopathies, and dystrophies associated with a Fukutin-Related Protein (FKRP) disorder, comprising: administering to a patient in need thereof an effective amount of at least one compound selected from the group consisting of phenylbutyrate suberoylanilide hydroxamic acid (SAHA) and 5azacytidine.

2. The method of claim 1, wherein the administration is by intramuscular, intraperitoneal, subcutaneous, oral, or intravenous route.

* * * * *